United States Patent
Hanelt et al.

[11] Patent Number: 5,827,449
[45] Date of Patent: Oct. 27, 1998

[54] LIQUID-CRYSTAL MIXTURES, PROCESS FOR THEIR PREPARATION AND THEIR USE

[75] Inventors: Eckhard Hanelt, Geltendorf; Christian Schierlinger, München; Franz-Heinrich Kreuzer, Martinsried, all of Germany

[73] Assignee: Consortium für elektrochemische Industrie GmbH, München, Germany

[21] Appl. No.: 839,634

[22] Filed: Apr. 15, 1997

[30] Foreign Application Priority Data

May 14, 1996 [DE] Germany ............... 196 19 460.1

[51] Int. Cl.[6] .................. C09K 19/32; C09K 19/36
[52] U.S. Cl. .................. 252/299.62; 252/299.7; 428/1
[58] Field of Search .............. 252/299.01, 299.62, 252/299.61, 299.7; 428/1

[56] References Cited

U.S. PATENT DOCUMENTS

| | | | |
|---|---|---|---|
| 4,996,330 | 2/1991 | Scherowsky et al. | 548/544 |
| 5,211,877 | 5/1993 | Andrejewski et al. | 252/299.01 |
| 5,362,315 | 11/1994 | Müller-Rees et al. | 106/493 |
| 5,502,206 | 3/1996 | Zahn et al. | 548/406 |

FOREIGN PATENT DOCUMENTS

| | | |
|---|---|---|
| 0302619 | 2/1989 | European Pat. Off. . |
| 0358208 | 3/1994 | European Pat. Off. . |
| 0601483 | 6/1994 | European Pat. Off. . |
| 0606940 | 7/1994 | European Pat. Off. . |
| 626386 | 11/1994 | European Pat. Off. . |
| 0685749 | 12/1995 | European Pat. Off. . |
| 773250 | 5/1997 | European Pat. Off. . |
| 4234845 | 4/1994 | Germany . |
| 4328785 | 3/1995 | Germany . |
| 4342280 | 6/1995 | Germany . |
| 4408171 | 9/1995 | Germany . |

OTHER PUBLICATIONS

H. Finkelmann et al., Macromol. Chem. 179, 829–832 (1978) "Synthesis of Cholesteric Liquid Crystalline Polymers".

W. Noll Chemistry and Technology of Silicones, Academic Press, Orlando Fla., 1968, pp. 191–239.

Derwent Abstract AN 95-321444[42] for DE 4408171, 1995.

Derwent Abstract AN 95-216450[29] for DE 4342280, 1995.

*Primary Examiner*—Shean C. Wu
*Attorney, Agent, or Firm*—Collard & Roe, P.C.

[57] ABSTRACT

Liquid-crystalline materials having a cholesteric phase with a pitch of less than 400 nm, comprising a) liquid-crystalline organosiloxanes containing dianhydrohexitol derivatives as chiral groups, and b) chiral monomeric additives which induce the same helicity as the respective liquid-crystalline organo-siloxanes.

16 Claims, 1 Drawing Sheet

LIQUID-CRYSTAL MIXTURES, PROCESS FOR THEIR PREPARATION AND THEIR USE

BACKGROUND OF THE INVENTION

1. Field of the Invention

The present invention relates to liquid-crystal mixtures, to a process for their preparation, and to their use.

2. The Prior Art

Cholesteric liquid crystals (CLCs) reflect circular-polarized electromagnetic radiation in a wavelength range which depends on the helical structure of the CLC. The central wavelength of the reflection band is determined by the pitch (p) of the helical structure, and the width of the band is determined by the optical anisotropy of the mesogens. The central wavelength of the reflection band, which is referred to below as the reflection wavelength, is dependent on the observation angle. It obeys the equation $\lambda = n \cdot p \cdot \cos \alpha$, where n is the mean refractive index of the CLC, and $\alpha$ is the angle between the incident ray and the axis of the cholesteric helix. The direction of rotation of the reflected light corresponds to the direction of rotation of the cholesteric helix. If the pitch of the helical structure is significantly shorter than the wavelength of the electromagnetic radiation, then an effective refractive index in a cholesteric layer perpendicular to the helix axis is produced by averaging the short and long half-axes of the refractive index ellipsoid of the rod-shaped mesogens, which are arranged with their molecular axis in planes perpendicular to the helix axis. The layer refractive index parallel to the helix axis is equal to the short principal axis of the refractive index ellipsoid of the mesogens. A CLC layer of this type acts on an electromagnetic wave as a uniaxially birefringent medium of negative optical anisotropy.

Cholesteric liquid-crystal mixtures contain one or frequently a plurality of optically active components for inducing a chiral structure. For example, cholesteric liquid-crystal mixtures can consist of a nematic base material and one or more optically active dopes. These produce in nematic materials either a right-handed or a left-handed twist, which determines the direction of rotation of the reflected circular-polarized light. A large number of optically active dopes which are suitable for certain applications are described in the literature.

For left-handed helical materials, recourse is frequently made to cholesterol compounds, which, in addition to chirality, provide sufficiently mesogenic properties to generate a stable mesophase. Examples of suitable compounds are the cholesterol derivatives disclosed in H. Finkelmann, H. Ringsdorf et al., in Makromol. Chem. 179, 829–832 (1978), or the tartarimide derivatives disclosed in U.S. Pat. No. 4,996,330 and EP-A-626 386. In the preparation of right-handed helical systems, recourse has hitherto generally been made to non-steroidal systems. These systems usually do not have adequate mesophase stability. A suitable right-handed helical steroid system is described in DE-A-42 34 845. However, the cholest-8(14)-en-3-ol (doristerol) described therein, and derivatives thereof, have the disadvantage of a complex synthesis and a high cost of preparation.

DE-A-43 42 280 and DE-A-44 08 171 describe crosslinkable, monomeric hexitol derivatives and mixtures of monomeric hexitol derivatives with other liquid-crystalline compounds. The monomeric hexitol derivatives can be used as monomeric dopes for the preparation of cholesteric networks. The hexitol-containing systems described therein are only accessible by complex syntheses. The monomeric hexitol derivatives described in DE-A-43 42 280 can be polymerized via vinyl or epoxide radicals. The mixtures of monomeric hexitol derivatives described in DE-A 44 08 171 can be crosslinked by free-radical or ionic polymerization processes.

It is known that liquid crystals consisting of organosiloxane structures carrying mesogenic side groups are distinguished over LC systems which do not contain siloxanes by the fact that, owing to the choice of the organosiloxane backbone, the molecular weight can be varied simply and virtually infinitely. This allows the liquid-crystalline properties, such as, for example, the phase behavior, the glass transition temperature and the clearing point, or, for example, also the viscosity, to be matched to the requirements in broad ranges.

It is also known that cholesteric liquid crystals consisting of organosiloxane structures carrying mesogenic side groups in which some of the side groups have been esterified by means of methacrylic acid can be aligned between two substrates and subsequently crosslinked.

For example, EP-A-358 208 (corresponds to U.S. Pat. No. 5,211,877), EP 0 626 386 A1 (corresponds to U.S. Pat. No. 5,502,206) and DE 42 34 845 A1 describe crosslinkable cyclic siloxanes containing mesogenic side groups in which some of the side groups have been esterified by means of methacrylic acid. The chiral substances incorporated into these polymers include hydrosilylated ω-olefin derivatives of cholesterol, doristerol or tartarimides. However, these chiral substances do not allow the preparation of cholesteric systems having an organosiloxane backbone having a stable liquid-crystalline phase with a pitch of less than 400 nm.

SUMMARY OF THE INVENTION

It is an object of the present invention to provide liquid-crystalline materials having a cholesteric phase with a pitch of less than 400 nm.

A further object of the invention was to provide films having a defined refractive index anisotropy for visible light and films having wavelength-selective and polarization-selective properties for electromagnetic radiation in the wavelength range between 100 nm and 400 nm (referred to as UV light below).

The first object is achieved by mixtures comprising a) liquid-crystalline organosiloxanes containing dianhydrohexitol derivatives as chiral groups, and b) chiral monomeric additives which induce the same helicality as the respective liquid-crystalline organosiloxanes.

The dianhydrohexitol derivatives are preferably at least one compound selected from the group consisting of dianhydrosorbitol, dianhydromannitol and dianhydroiditol.

-continued and where R and S define the absolute configuration on the respective carbon atom, in accordance with the R/S nomenclature of Cahn, Ingold and Prelog.

The liquid-crystalline organosiloxanes in the novel liquid-crystalline mixtures preferably contain, per molecule, at least one Si-c-bonded dianhydrohexitol derivative of the general formula (1)

$$M^1\text{---hexitol---}M^2 \tag{1}$$

as chiral component, where
hexitol is one of the above dianhydrohexitol groups,
$M^1$ is a radical of the general formula (2), (2) and $M^2$ is a radical of the general formula (2) or a radical of the general formula (3), (3)

where, in the above general formulae (2) and (3), $R^1$ and $R^3$ are each a radical of the formula $C_nH_m$, in which one or more non-adjacent methylene units may be replaced by oxygen atoms or dimethylsilyl radicals, $R^2$ is a polymerizable ethylenically unsaturated group or alkoxysiloxy group or cholesteryl radical, doristerol radical, halogen atom, hydrogen atom, hydroxyl, nitrile or trialkylsiloxy group whose alkyl radicals each have 1 to 8 carbon atoms, $A^1$, $A^2$, $A^3$ and $A^4$ are identical or different divalent radicals, namely 1,4-phenylene, 1,4-cyclohexylene, substituted arylene having 1 to 10 carbon atoms, substituted cycloalkylene having 1 to 10 carbon atoms or heteroarylene having 1 to 10 carbon atoms, $X^1$ and $x^2$ are identical or different divalent radicals from the group consisting of —OCO—, —NHCO—, —CO— and a radical $R^1$, $Z^1$ and $Z^2$ are identical or different divalent radicals from the group consisting of —$(CH_2)_q$—, —COO—, —CH=CH— —N=N—, —N=N(O)—, —OCO—, —$CH_2CO$—, —$COCH_2$—, —$CH_2$—O—, —O—$CH_2$—, —$CH_2$—NH—, —NH—$CH_2$—, —CONH—, —NHCO—, —N=CH— and —CH=N—, a, b, c and d are identical or different integers, each having a value of 0, 1, 2 or 3, n is an integer having a value of from 0 to 20, m has the value 2n or, if n is at least 2, can also have the value (2n–2), q is an integer having a value of 1, 2 or 3, and r and s are each an integer having a value of 0 or 1.

The liquid-crystalline organosiloxanes in the novel mixtures are preferably built up in accordance with the general formulae (4) to (6)

(4)

(5)

(6)

in which
B is a radical of the general formula (1) and, if desired, a radical of the general formula (7)

(7)

where, in the above formulae (4) to (7), the radicals R are identical or different, unsubstituted or substituted $C_1$- to $C_{18}$-hydrocarbon radicals, e and g are each an integer having a value of from 1 to 100, f, h, i and j are each an integer having a value of from 0 to 100, $R^4$ is as defined for $R^1$, $A^5$, $A^6$ and $A^7$ are as defined for $A^1$, $Z^3$ and $Z^4$ are as defined for $Z^1$, $A^8$ is a saturated or olefinically unsaturated, unsubstituted or substituted alkyl, alkoxy or cycloalkyl radical, in each case having 1–16 carbon atoms, cholestan radical, cholesteryl radical, doristerol radical, halogen atom, hydrogen atom, hydroxyl, nitrile, (meth)acryloxy, (meth)acryloxyethyleneoxy, (meth)acryloxydi(ethyleneoxy), (meth)acryloxytri-(ethyleneoxy), R- or S-tetrahydrofurancarboxylate or trialkyl- or trialkoxysiloxy group whose alkyl or alkoxy radicals have 1 to 8 carbon atoms, x, y and z are identical or different integers, each having a value of 0, 1, 2 or 3, and t and u are as defined for r, with the provisoin that the sum e+f is at least 2.

Examples of $R^1$, $R^3$ and $R^4$ are linear or branched, saturated, divalent alkyl radicals, which may be interrupted or replaced by $[O(CH_2)_v]_w$ units, where v and w are preferably identical or different integers, each having a value of 1, 2, 3 or 4. The $[O(CH_2)_v]_w$ unit can, for example, be an ethylene glycol-propylene glycol block copolymer.

In particular, n has a value of 3, 4, 5 or 6, and m preferably has the value 2n.

The polymerizable, ethylenically unsaturated groups $R^2$ can, for example, be methacryloxy, acryloxy, vinyloxy, ethyleneoxy or styryl groups. Examples of alkoxysiloxy groups $R^2$ are trialkoxysilyloxy and alkyldialkoxysiloxy groups whose alkyl and alkoxy radicals have 1 to 8 carbon atoms. Examples of suitable alkyl radicals and the alkyl radicals present in the alkoxy radicals are listed below under the radicals R. The alkyl and alkoxy radicals preferably have 1, 2 or 3 carbon atoms.

Preferred substituents for the substituted arylene and substituted cycloalkylene radicals $A^1$, $A^2$, $A^3$, $A^4$, $A^5$, $A^6$ and $A^7$ are halogen atoms, $C_1$- to $C_4$-alkyl and alkoxy radicals, nitro groups and cyano groups.

The sums a+b and c+d are preferably each 1 or 2.

Examples of R are alkyl radicals, such as the methyl, ethyl, n-propyl, isopropyl, n-butyl, isobutyl, tert-butyl, n-pentyl, isopentyl, neopentyl and tert-pentyl radicals; hexyl radicals, such as the n-hexyl radical; heptyl radicals, such as the n-heptyl radical; octyl radicals, such as the n-octyl radical and isooctyl radicals, such as the 2,2,4-trimethylpentyl radical; nonyl radicals, such as the n-nonyl radical; decyl radicals, such as the n-decyl radical, dodecyl radicals, such as the n-dodecyl radical; octadecyl radicals, such as the n-octadecyl radical; alkenyl radicals, such as the vinyl, allyl and 3-butenyl radicals; cycloalkyl radicals, such as cyclopentyl, cyclohexyl, cycloheptyl and methyl-cyclohexyl radicals; aryl radicals, such as the phenyl, naphthyl, anthryl and phenanthryl radicals; alkaryl radicals, such as o-, m- and p-tolyl, xylyl and ethyl-phenyl radicals; and aralkyl radicals, such as the benzyl radical and the α- and β-phenylethyl radicals. Preferred substituents for the substituted hydrocarbons are halogen atoms, or nitro or cyano groups.

Preferred radicals R are $C_1$- to $C_{10}$-alkyl radicals and phenyl radicals, in particular methyl radicals.

Suitable halogen atoms are fluorine, chlorine, bromine and iodine, in particular fluorine, chlorine and bromine.

e and g are preferably each an integer having a value of at least 1, in particular at least 2. f, h, i and j are preferably each an integer from 0 to 35. The sum e+f is preferably at least 4 and at most 15. The sum g+h is preferably at least 2 and at most 35. The sum i+j is preferably at most 10.

Examples of suitable saturated or olefinically unsaturated $C_1$- to $C_{16}$-alkyl, -alkoxy or -cycloalkyl radicals $A^8$ are listed above under the radicals R. The alkyl and alkoxy radicals preferably have 1 to 8 carbon atoms.

Examples of substituted radicals $A^8$ are cyano-alkyl radicals, such as the 2-cyanoethyl radical, haloalkyl radicals, in particular perfluoroalkyl radicals, such as heptafluoropropyl radical, haloaryl radicals, such as the o-, m- and p-chlorophenyl radical, and cyanoaryl radicals, such as the cyanophenyl radical.

Preferred substituents are halogen atoms, the nitro group and the cyano group.

The sum x+y+z is preferably 1, 2 or 3.

The sum t+u is preferably 1 or 2.

Preferred compounds of the general formula (1) are the dianhydrohexitol derivatives in which $M^1$, namely the general formula (2), has the general formula (8)

(8)

in which o is the number 3 or 4, and $Z^1$, $A^2$, $X^1$, r and b are as defined above.

Hexitol is preferably dianhydrosorbitol or dianhydromannitol.

Particularly preferred compounds of the general formula (7) are those of the general formula (9)

(9)

in which p is the number 3 or 4, and

$Z^3$, $Z^4$, $A^6$, $A^7$, $A^8$, t, u, y and z are as defined above.

t preferably has the value 1, and y and z each preferably have the value 0 or 1. If y has the value 1, u can have the value 0 or 1, and if y has the value 0, u has the value 0.

The liquid-crystalline organosiloxanes containing dianhydrohexitol derivatives can be prepared by reacting organosiloxanes and/or organosilanes which can be condensed to form organosiloxanes with alkenes or alkynes of the general formula (1) and, if desired, of the general formula (7) which contain mesogenic groups, where the organosiloxanes and at least some of the organosilanes contain at least one hydrogen atom bonded directly to silicon.

In a preferred process for the preparation of liquid-crystalline organosiloxanes of the preferred general formulae (4)–(6) above containing dianhydrohexitol derivatives, organosiloxanes of the general formulae (10) to (12)

(10)

(11)

(12)

and/or organosilanes of the general formula (13)

$HRSiY^1Y^2$ (13)

are reacted with compounds of the general formula (14)

$M^3$—hexitol—$M^2$ (14)

and, if desired, compounds of the general formula (15)

$R^5-(A^5)_x-Z^3_t-(A^6)_y-Z^4_u-(A^7)_z-A^8$ (15)

and, if organosilanes of the general formula (13) are used, the resultant organosilanes of the general formula (16)

$BRSiY^1Y^2$ (16)

are condensed, where, in the above formulae (10) to (16), $M^3$ is a radical of the general formula (17)

$R^6-(A^1)_a-Z^1_r-(A^2)_b-X^1-$ (17)

$Y^1$ is a condensable group, $Y^2$ is a condensable group or a radical R, $R^5$ and $R^6$ are each a radical of the formula $C_\alpha H_\beta$, in which one or more non-adjacent methylene units may be replaced by oxygen atoms or dimethylsilyl radicals, and where α is as defined for n and

β has the value 2α–1 or 2α–3, and

R, $M^2$, $A^1$, $A^2$, $A^5$, $A^6$, $A^7$, $A_8$, $Z^1$, $Z^3$, $Z^4$, B, $X^1$, a, b, e, f, g, h i, j, t, u, r, x, y and z are as defined above.

$Y^1$ and $Y^2$, if $Y^2$ is not R, are preferably a halogen atom or a $C_1$- to $C_4$-alkoxy group, in particular a chlorine atom or a methoxy or ethoxy group.

In the above general formulae (15) and (17), $R^5$ and $R^6$ are terminally unsaturated. α preferably has a value of from 3 to 7, in particular a value of 3 or 4.

Particularly preferred compounds of the general formula (15) are those of the general formula (18)

in which

K is the number 1 or 2, and $Z^3$, $Z^4$, $A^6$, $A^7$, $A^8$, t, u, y and z are as defined above.

The compounds of the general formulae (14) and (15) can be hydrosilylated directly on hydrogen atoms bonded to silicon.

The preferred values and sums for e, f, g, h, i and j given above for the general formulae (4) to (6) also apply to the general formulae (10) to (12). The reaction of organosiloxanes containing hydrogen atoms bonded directly to silicon and/or organosilanes which can be condensed to give organosiloxanes with alkenes or alkynes of the general formulae (14) and (15) is carried out in a manner known per se, for example by hydro-silylation in solvents, such as hydrocarbons, ethers or esters, using platinum group metals or compounds as catalyst. Suitable hydrosilylation processes are described, for example, in EP-A-358 208 (corresponds to U.S. Pat. No. 5,211,877). In a preferred process, from 0.1 to 10 mol, in particular from 0.2 to 2 mol, of compounds of the general formulae (1) to (7) are employed in the hydrosilylation per gram-atom of hydrogen atoms bonded directly to silicon atoms.

If the process outlined above is carried out using organosilanes, for example of the general formula (13), these are condensed together with organosilanes or organosiloxanes containing dianhydrohexitol derivatives of the general formula (1) by processes known per se to give liquid-crystalline organosiloxanes. This can be carried out, inter alia, by reaction with acids, such as aqueous hydrochloric acid. Such processes are described in W. Noll, Chemistry and Technology of Silicones, Academic Press, Orlando, Fla., 1968, pages 191 to 239. The reactions described give a mixture of various molecules.

The dianhydrohexitol derivatives can be synthesized, for example, by the following process: dianhydrohexitol is esterified by processes known per se using a carboxylic acid or a carboxylic acid chloride into which an olefinic or acetylenic group has already been introduced by processes known in organic chemistry, in an inert solvent at room temperature or at elevated temperature, if necessary with addition of activating, water-binding or acid-binding auxiliaries.

The liquid-crystalline organosiloxanes containing dianhydrohexitol derivatives as chiral group which are present in the novel liquid-crystal mixture have a significantly greater optical twisting power per dianhydrohexitol group than do the steroid- and tartarimide-containing liquid-crystalline organosiloxanes described hitherto.

Thus, substitution of an ω-olefin derivative of cholesterol, doristerol or tartarimide in known siloxanes by a dianhydrohexitol derivative allows the wavelength of the organosiloxane to be shifted toward shorter wavelengths.

Depending on the other compounds hydrosilylated onto the organosiloxane, the cholesteric phase of the liquid-crystal mixture can be stabilized by alignment at room temperature, by alignment at above the glass transition temperature and subsequent quenching into the glass state or by alignment and subsequent polymerization at room temperature or elevated temperature. In addition to the dianhydrohexitol derivatives, the liquid-crystalline organosiloxanes (component a) preferably contain, as chiral component, other mesogenic radicals which enable subsequent free-radical or ionic cross-linking.

In addition to the organosiloxane derivatives described above, the novel LC mixtures contain monomeric, chiral additives which induce the same helicality as the organosiloxane derivatives (component b) present in each case.

The monomeric chiral additives are preferably compounds of the formula (19) or (20)

in which $M^4$ and $M^5$ are a radical of the general formula (2) or a radical of the general formula (3), and chir is a chiral radical, such as a cholesteryl, dihydrocholesteryl, doristeryl, cholestadienyl or stigmasterol group, and hexitol, $M^2$, $R^1$, $R^2$, $R^3$, $A^1$, $A^2$, $A^3$, $A^4$, $X^1$, $X^2$, $Z^1$, $Z^2$, a, b, c, d, r and s are as defined above.

$M^4$ is preferably a radical of the general formula (3); very particular preference is given to radicals of the general formula (3) in which $R^2$ is an ethylenically unsaturated, polymerizable group.

The novel mixtures may additionally contain achiral, monomeric substances which have no significant adverse effect on the liquid-crystalline phase.

These components preferably contain at least one ethylenically unsaturated group and can therefore be polymerized. Such mixture components can be, for example, ethylene glycol di(meth)acrylate, polyethylene glycol di(meth) acrylates, propanediol di(meth)acrylate, butanediol di(meth) acrylate, hexanediol di(meth)acrylate, trimethylolpropane tris(meth)acrylate, divinylbenzene, styrene and substituted styrenes, hydroquinone bis(meth)acrylate, 4-alkylphenyl (meth)acryloylbenzoates, 4-alkoxyphenyl (meth) acryloylbenzoates and (meth)acryloylphenyl 4-allyloxybenzoate.

The liquid-crystalline mixtures containing dianhydrohexitol derivatives can be used to induce either a right-handed or a left-handed helical structure. These left-handed or right-handed helical, liquid-crystalline organosiloxanes and the LC mixtures containing these organosiloxanes exhibit selective reflection of left-handed or right-handed polarized light. By changing the content of chiral dianhydrohexitol-containing radicals or the content of monomeric chiral additives, the selective reflection wavelength can be adjusted.

The high optical twisting power of the dianhydrohexitol derivatives means that it is generally sufficient to replace 1–20% of the mesogenic radicals of an organosiloxane by a dianhydrohexitol derivative in order to achieve a pitch of less than 400 nm in the novel LC mixture.

The novel mixtures are preferably prepared by combining the components in the solid or liquid phase or in solution.

The liquid-crystalline mixtures of components containing methacryloxy and/or acryloxy groups can be polymerized by processes known per se and also crosslinked given a suitable choice of the components.

The liquid-crystalline mixtures which contain methacryloxy and/or acryloxy groups in the mesogenic radicals of the general formulae (1) and/or (7) and/or (19) and/or (20) can be three-dimensionally crosslinked. This crosslinking is preferably achieved by means of free radicals generated by peroxides, by UV light, by electromagnetic radiation with greater energy than UV light, by beams of charged particles or thermally. It can also be carried out cationically or anionically. The crosslinking can also be achieved by means of crosslinking agents containing hydrogen atoms bonded directly to silicon atoms with catalysis by the abovementioned platinum-metal catalysts. Particular preference is given to crosslinking with the aid of UV light. This crosslinking is described, for example, in EP-A-358 208 (corresponds to U.S. Pat. No. 5,211,877).

The further object of the invention is achieved by optically anisotropic films which consist of the novel LC material.

The present invention furthermore relates to a process for the production of such films.

The optically anisotropic films are preferably produced by a process in which the novel LC mixture is applied to a substrate surface and aligned. The LC layer may be covered by a second substrate. The alignment of the mesogens is achieved, for example, by shearing the material during application or, for example, after application by interaction of the mesogens with the appropriately selected substrate surface(s) or by an electric field.

The LC mixture is preferably aligned in a temperature range of from above the glass transition temperature to below the commencement of clearing of the particular LC mixture. In order to facilitate a simple industrial process, the composition of the LC mixture is preferably balanced in such a way that the alignment temperature is between 20° C. and 150° C.

The mesogens in this optically anisotropic film preferably have a helical alignment similar to a liquid-crystalline cholesteric phase. The pitch of the helical structure is preferably between 100 nm and 400 nm, but may also be greater if the concentration of the chiral components is lower.

The axis of the helix can be parallel to the film surface; or perpendicular to the film surface; or tilted at an angle between 0° and 45° to the surface perpendicular. The mean alignment of the mesogens in the vicinity of the film surface can be parallel or perpendicular to the film surface or inclined at an angle of between 0° and 90° to the film surface.

Substrates which can be used are all materials which are known for the production of optical elements. Preference is given to transparent or semitransparent substrates, such as many organic or inorganic substrates. The substrates can be planar or curved.

Particular preference is given to substrates whose physical properties do not change at the production, processing and use temperatures of the LC films.

Very particular preference is given to glass and quartz platelets and polymer films, such as, for example, polycarbonates, polysulfones, polyethylene terephthalates and polyimides.

If necessary, the substrate(s) can be provided with an additional alignment aid, for example a layer of polyimide, polyamide, polyvinyl alcohol or a silicon oxide ($SiO_x$).

The alignment layer can be produced by known coating, printing or immersion processes described a number of times in the literature. The alignment layers or the substrates can be given an additional treatment, for example rubbing, to provide a surface structure which favors alignment. Suitable processes for achieving a tilt between the mesogens of a liquid-crystalline phase and their interfaces are described in the literature, for example vapor-deposition of inorganic materials at an oblique angle.

The novel LC mixture can be applied to the substrate surface in solution or as a solvent-free dry material above the glass transition temperature, for example by spin coating, by means of a knife coater or a roll.

The thickness of the LC layer is preferably greater than three times the pitch up to a maximum of 100 $\mu$m. Layer thicknesses of between 1 $\mu$m and 20 $\mu$m are particularly preferred.

The application and the alignment of the LC mixture can be carried out fully continuously, semi-continuously or discontinuously. A particularly preferred fully continuous process is that described in EP-0 601 483 A1.

After the alignment operation, the LC mixture is cooled to below the glass transition temperature or, if the LC mixture contains ethylenically un saturated, polymerizable groups, is preferably crosslinked.

The crosslinking is preferably achieved by means of free radicals generated by peroxides, by UV light, by electromagnetic radiation with greater energy than UV light, by beams of charged particles or thermally. It can also be carried out cationically or anionically. The crosslinking can also be achieved by means of crosslinking agents containing hydrogen atoms bonded directly to silicon atoms with catalysis by the abovementioned platinum-metal catalysts. Particular preference is given to crosslinking by UV light using a photoinitiator.

The resultant film can be used together with the substrate in the form of a laminate, as a film which is open on one side or, after removal of the substrates, as a free film. The film is preferably used together with the substrate or as a film which is open on one side.

The invention furthermore relates to optically anisotropic CLC platelets containing the novel LC materials.

EP 0 601 483 A1 describes how CLC pigments which reflect visible light can be prepared by detaching a polymerized cholesteric film from the substrate and subsequently comminuting the resultant crude lumps. Optically anisotropic CLC platelets having a pitch which is shorter than the wavelength of visible light can be produced analogously from the novel films.

The CLC platelets can be incorporated into a suitable binder system as described, for example, in EP 0 685 749 A1. The invention therefore likewise relates to binder systems containing the novel LC platelets.

Like the novel films, the CLC platelets produced therefrom also have a defined refractive index anisotropy for visible light or a wavelength- and polarization-selective reflection for UV light. The optical properties required of suitable binder systems accordingly depend on the particular application.

In applications which utilize the selective reflection of the CLC platelets in the UV region, UV-transparent binders are preferably employed. By contrast, binders which are colorless and transparent to visible light are preferred for applications which utilize the optical anisotropy in the region of visible light.

For optical elements, preference is given to using binder systems whose mean refractive index after curing is similar to the mean refractive index of the CLC platelets.

In order to produce durable layers containing CLC platelets, curable binder systems are preferably suitable. For specific applications, for example UV-protection layers, however, use can also be made of non-curable binders, such as, for example, oils and pastes.

Particular preference is given to binder systems which do not affect the physical properties of the CLC platelets or only do so in a defined manner.

Examples of suitable binder systems are polymerizable resins (UP resins, silicone resins and epoxy resins), dispersions, solvent-containing surface coatings or waterborne surface coatings, polyermizable LC silicones or all transparent plastics, for example polyvinyl chloride, polymethyl methacrylate and polycarbonate.

In addition to these isotropic binders, liquid-crystalline systems can also be used as binder, for example liquid-crystalline polymers or polymerizable liquid-crystalline resins, and polymerizable LC silicones.

In order to produce a layer or a film having specific optical properties, the CLC platelets are stirred into a liquid binder. The platelets are aligned parallel to the surface of the layer as in surface coating with liquid-crystalline colored pigments (see, for example, EP 0 601 483 A1 (corresponds to U.S. Pat. No. 5,362,315) or EP 0 685 749 A1) during application of a thin layer of the pigment/binder mixture to a substrate or during extrusion of the mixture. Depending on the requirements of the particular application, the film can be detached from the substrate after the binder has cured.

The novel LC mixtures containing the liquid-crystalline dianhydrohexitol derivatives and chiral monomeric additives of the same chirality, and the optically anisotropic films and CLC platelets produced therefrom, are suitable, owing to their selective reflection in the UV region or their anisotropic optical properties in the region of visible light, for many applications, some of which are mentioned below by way of example.

Novel LC mixtures, films or platelets can be used, for example, to produce optical elements, such as wavelength- and polarization-selective mirror layers for electromagnetic radiation in the UV region or retardation films for visible light.

The novel LC mixtures, films or platelets are particularly suitable for the production of layers for improving the viewing-angle dependence of LCDs, in particular of TN cells.

The invention therefore likewise relates to wavelength-selective and polarization-selective optical elements for UV light and optical retardation films for visible light which contain the novel materials.

For the applications described, the organosiloxane component of the novel LC mixtures can be either liquid-crystalline organosiloxanes containing mixtures of the dianhydrohexitol derivatives with one another or mixtures of the organosiloxanes with other liquid-crystalline materials. Chiral monomer components which can be used are both mixtures of the chiral monomers with one another and also mixtures of the chiral monomers with other materials which do not adversely affect the LC properties.

The improvement in the viewing-angle dependence of TN cells by means of the novel LC materials is described in greater detail below.

The classical application of TN cells is in simple segmented display devices, for example in pocket calculators and electronic watches. As the development of thin-film technology proceeds and integration of the addressing electronics increases, TN cells have become competitive even in complex display devices, for example colored display screens. In TFT-LCDs each pixel on the screen is represented by an individual TN cell which is switched by its own thin-film transistor (TFT) or a diode. TFT-LCDs are distinguished by particularly good contrast and fast response times. However, the good contrast is only present in a small viewing-angle range perpendicular to the screen plane. The main reason for the drop in contrast at acute viewing angles is the viewing-angle dependence of the optical retardation in the liquid-crystal cell in the switched state, i.e. with a voltage applied.

In order to broaden the range of applications of TFT-LCDs, the reduction in the viewing-angle dependence is of central importance. This can be achieved, for example, by compensating for the birefringence of the light in the switched cell. The LC filling in a TN cell has a positive optical anisotropy in an electric field. In liquid-crystal displays which appear transparent in the unswitched state, i.e. without an electric field, the contrast can be improved for large viewing angles by compensating for the positive optical anisotropy of the switchable cell in the dark state using an additional layer of negative optical anisotropy which is installed between the liquid-crystal cell and the polarizer. One design of this principle is the UST compensator, in which the negative optical anisotropy is achieved by means of a cholesteric liquid-crystal layer having a reflection band in the ultra-violet region. The pitch of the helical structure in the cholesteric liquid crystal must be sufficiently small that the optical activity of the layer for visible light is negligible. Such compensators have hitherto been achieved by means of cells filled with liquid-crystalline monomers or by means of liquid-crystalline polymers having a cholesteric phase which are rapidly cooled to below the glass transition temperature after alignment.

However, low-molecular-weight systems and most polymers are of only limited utility for compensation of the viewing-angle dependence of liquid-crystal displays. The cells filled with liquid-crystalline monomers have the disadvantage that, owing to the requisite thickness, they result in parallax errors, that they considerably increase the weight of an LCD and that they are too expensive to manufacture. Liquid crystals consisting only of monomers which can be crosslinked after alignment are generally more difficult to handle than polymers, since their alignment is affected more by the processing temperature. If liquid-crystalline polymers which cannot subsequently be crosslinked are used, it is necessary for them to have a glass transition temperature well above room temperature so that the alignment remains stable after quenching into the glass state. The processing and alignment of these polymers must be carried out at elevated temperatures, which is disadvantageous from a technical point of view and makes the process more expensive.

The novel liquid-crystal mixture having a pitch which is shorter than the wavelength of visible light can be used to produce relatively simply, as described above, durable films which, owing to their negative optical anisotropy, are ideally suited for use as UST compensators. For this purpose, preference is given to a liquid-crystal mixture which appears totally transparent and colorless to visible light. It is not necessary for the LC mixture to be transparent to UV light too.

The liquid-crystal mixture, which preferably contains polymerizable, ethylenically unsaturated groups, is, for this purpose, preferably applied to one or between two optically transparent substrates, aligned and subsequently polymerized. In order optimally to compensate for the asymmetric viewing-angle dependence of the LCDs, the LC mixture is preferably aligned in such a way that the axis of symmetry of the negative refractive-index ellipsoid is tilted at an angle of between 0° and 45° to the surface perpendicular of the retardation layer, depending on the properties of the particular LCD.

Use of novel CLC platelets allows the production of retardation films of negative optical anisotropy, for example for improving the viewing-angle dependence of LCDs, to be considerably simplified, since the known processes for the production of plastic films can be used. To this end, a mixture of the platelets with a binder system is prepared, applied to a substrate, preferably as described above, and subsequently cured.

The present invention likewise relates to a liquid-crystal display device (LCD) which contains at least one example of the novel optically anisotropic film or a novel retardation film based on optically anisotropic CLC platelets or a laminate with this film or the retardation film.

The display device furthermore contains a cell which is filled with a monomeric liquid crystal (LC) whose optical activity or retardation can be switched electrically by applying a voltage. To this end, two opposite walls of the cell (front and back) are provided with electrodes, of which at least the electrode on the front is optically transparent. The mesogens in the monomeric LC filling have a positive dielectric anisotropy. Without an electric field, the alignment of the mesogens in the cell is parallel to the front and back or tilted at an angle of less 20° to the front or back. The alignment of the mesogens at the front is twisted with respect to the mesogens at the back by an angle of between 60° and 300° about an axis perpendicular to the front. The axis of this helical structure is perpendicular to the front and back of the cell. The helical structure can be achieved by means of alignment layers on the front and back of the cell and by doping the monomeric LC filling with chiral monomers. By applying an electric voltage to the cell, the mesogens in the LC filling are twisted with their optical axis in the direction of the electric field lines, giving the LC filling of the cell a positive optical anisotropy with the optical axis approximately in the direction of the helix axis. The LCD contains on the front at least one polarizer which is optically transparent and acts in the transmission direction. A second optically transparent polarizer or a polarization-selective reflector can be located on the back. The angle between the optical axes of the two polarizers is matched to the desired switching properties of the LCD.

Examples of specific embodiments of the arrangement described here without the novel film are TN cells in which the mesogens in the switchable cell are twisted by 90° or STN cells in which the twist is between 180° and 300°.

Another example of an LCD which contains at least one example of the novel optically anisotropic film or of a novel retardation film based on optically anisotropic CLC platelets or of a laminate with this film or the retardation film differs from the above-described LCD in that the alignment of the mesogens at the front of the switchable cell filled with a monomeric liquid crystal of positive dielectric anisotropy is essentially parallel to the mesogens at the back of the cell.

In order to be able electrically to switch the optical activity or retardation of the cell by applying a voltage, two opposite walls of the cell (front and back) are provided with electrodes, on which at least the electrode on the front is optically transparent. Without an electric field, the alignment of the meosgens in the cell is parallel to the front and back or tilted at an angle of less than 20° to the front or back. By applying an electric voltage to the cell, the mesogens in the LC filling are twisted with their optical axis in the direction of the electric field lines, resulting in the LC filling of the cell experiencing a change in its positive optical anisotropy. The LCD contains on the front at least one polarizer which is optically transparent and acts in the transmission direction. A second optically transparent polarizer or a polarization-selective reflector can be located on the back. The angle between the optical axes of the two polarizers is matched to the desired switching properties of the LCD.

A further LCD which contains at least one example of the novel optically anisotropic film or of a novel retardation film based on optically anisotropic CLC platelets or of a laminate with this film or the retardation film differs from the above LCDs in that the switchable LC cell is filled with a monomeric liquid crystal of negative dielectric anisotropy. Without an electric field, the mesogens in the cell are homeotropic, i.e. aligned perpendicular to the cell walls carrying the electrodes. This is achieved, for example, by means of a suitable surface treatment of the cell walls. At least the electrodes on the front of the cell are optically transparent. By applying an electric voltage to the cell, the mesogens in the LC filling are twisted with their optical axis in a direction perpendicular to the electric field lines, and the optical activity or retardation of the cell is thus switched. The LCD contains on the front at least one polarizer which is optically transparent and acts in the transmission direction. A second optically transparent polarizer or a polarization-selective reflector can be located on the back. The angle between the optical axes of the two polarizers is matched to the desired switching properties of the LCD.

In all the liquid-crystal displays described above which are known in the prior art without a novel optically anisotropic film or retardation film based on CLC platelets, the novel optically negative anisotropic film or a laminate of this film with a substrate or the retardation film based on optically anisotropic CLC platelets is preferably installed relative to the LC filling in such a way that the polarizer(s) is (are) outside the LC cell and the novel film.

The novel optically anisotropic film or the retardation film based on optically anisotropic CLC platelets can be arranged on the front or back or on both sides of the switchable LC cell. It can also be applied directly to the outside or inside of the cell walls. In this case, the cell walls can serve as substrate for the production of a novel film.

Applications are described below of the novel films or CLC platelets which utilize the wavelength- and polarization-selective reflection of electromagnetic radiation in the wavelength range between 100 nm and 400 nm.

The wavelength range in which the novel films or CLC platelets reflect circular-polarized light is dependent on the proportion of chiral mesogens. Since many organic materials absorb UV light, absorption in the film should also be noted in this application. The reflection is based on an interference effect, in which the electro-magnetic wave penetrates into the film by on average a few pitches of the helical structure. The distance travelled in the film is therefore a few $\mu$m. By means of a suitable composition of the novel liquid-crystal mixture, for example replacement of phenyl groups by cyclohexane groups, the absorption of electromagnetic radiation in the region of the cholesteric UV reflection band can be reduced, preferably in the wavelength range from 200 nm to 400 nm. It is also possible to achieve the situation that the novel films or CLC platelets appear optically transparent and colorless to visible light.

The novel film or the CLC platelets produced therefrom can be used to produce safety and other markings which, owing to their good reflection in the UV region, can be recorded particularly well by instruments containing UV detectors. For this application, the CLC platelets are preferably applied in a UV-transparent binder to a substrate to be marked. Use of the embodiment of the novel films or CLC platelets which are optically transparent and colorless to visible light allows the production of markings which are invisible to the human eye. The invention thus also relates to markings, in particular safety markings, which contain the novel LC mixture.

A further application of the novel films and UV platelets is a reflective UV-protection film or UV-protection paint. The principal advantage of a reflective UV-protection layer compared with the absorptive UV-protection layers that are used almost exclusively is that the reflection is based on an interference effect which, in contrast to absorption, does not result in a gradual destruction of the material.

For this application, preference is given to a novel liquid-crystal mixture which has only low absorption in the wavelength range which is important for the specific protection function. For example, a wavelength range of from about 290 nm to 380 nm is appropriate for protection against the UV content of sunlight on the ground. The requisite band width of UV protection can be set, for example, by the methods described in EP 0 606 940. The left-handed and right-handed helical components of the UV light are reflected back independently of one another by use of in each case at least one novel left-handed and right-handed helical cholesteric film or by a mixture of novel left-handed and right-handed helical UV platelets in a binder which is transparent to UV light.

Examples of such binders are given above. The novel liquid-crystal mixtures facilitate, in particular, the production of UV-protection layers which are transparent and colorless to visible light. These are suitable, for example, for protection of the human skin and the eyes. Examples of possible use forms are suncreams and sunglasses.

This invention furthermore relates to a wave-length-and polarization-selective band filter and reflector for UV light, preferably for electromagnetic radiation in the wavelength range from 200 nm to 400 nm, which consists of the novel material, preferably in the form of a film or platelets made from this film. This band filter or reflector for UV light may additionally have imaging properties.

DE 43 28 785 A1 describes how wavelength- and polarization-selective imaging elements can be produced using cholesteric liquid crystals for visible light to the near UV. A planar filter comprising cholesteric liquid crystals is described in EP-A-302 619. The use of CLC platelets for optical elements having color- and polarization-selective reflection is described in EP 0 685 749 A1. The novel mixtures can be used analogously.

If the novel film is prepared between two substrates, at least one of the substrates must, for this application, be optically transparent in the UV region. This restriction does not apply when films which are open on one side are used if the open side is used as a reflector for UV light. For use of CLC platelets, it is necessary that the binder system used is also transparent in the UV region.

The helical structure of the novel films having a pitch of from 100 nm to 400 nm results in the reflection of either left-handed or right-handed circular-polarized UV light within a band width of, typically, from 10 nm to 40 nm. This band width can be increased by additional measures, for example using the methods described in EP 0 606 940 for modifying the pitch along the layer thickness.

The novel film or a layer made from novel CLC platelets in a binder is thus suitable, for example, as a beam splitter for UV light. In the direction of the axis of the helical structure, the film has no birefringence for visible light. It is thus possible to use the novel films or platelets to produce specific optical components for UV light which appear optically transparent and colorless to visible light.

The imaging properties for UV light are achieved by using curved surfaces as substrate for the production of novel films. Likewise, novel CLC platelets in a UV-transparent binder can be applied to curved substrates. The curvature of the substrate surface used is determined in accordance with the requisite imaging properties by the known laws of ray optics. In order to keep the absorption of UV light in the film low, curved mirrors, for example concave and convex mirrors, are particularly preferred forms of optical elements for UV light. The CLC layer made from novel material is aligned in such a way that the helix axis is perpendicular to the curved substrate surface. If the CLC layer is aligned between two substrates as described in DE 43 28 785 A1, at least one of the substrates must then be transparent to UV light. If films which are open on one side are used on curved substrates, for example for use as curved mirrors, this restriction does not apply.

BRIEF DESCRIPTION OF THE DRAWINGS

Other objects and features of the present invention will become apparent from the following detailed description considered in connection with the accompanying drawing which discloses several embodiments of the present invention. It should be understood, however, that the drawing is designed for the purpose of illustration only and not as a definition of the limits of the invention.

In the drawing, wherein similar reference characters denote similar elements throughout the several views.

Other objects and features of the present invention will become apparent from the following Examples, which disclose the embodiments of the present invention. It should be understood, however, that the Examples are designed for the purpose of illustration only and not as a definition of the limits of the invention.

The examples below serve to illustrate the invention in greater detail:

EXAMPLE 1

Preparation of the dianhydrohexitol derivatives

The dianhydrohexitol derivatives 1–5 were prepared by the following general procedure:

24 mmol of isosorbide and 48 mmol of an ω-alkenyloxy- or ω-alkynyloxy-acid chloride are dissolved in 40 ml of toluene, and the mixture is refluxed for 12 hours. The toluene is distilled off in vacuo, and the crude product recrystallized from ethanol or isopropanol.

1)

Isosorbide bis(4-allyloxybenzoate)

2)

Isomannide bis(4-allyloxybenzoate)

3)

Isosorbide bis[4-(4-allyloxyphenyl)benzoate]

4)

Isosorbide bis[4-(3-butenyloxy)benzoate]

5)

Isosorbide bis(4-propargyloxy)benzoate

EXAMPLE 2

Preparation of the illustrative mixtures
Preparation of illustrative mixture 1

0.33 g (1.4 mmol) of tetramethylcyclotetrasiloxane and 1.09 g (2.0 mmol) (40 mol %) of cholesterol 4-allyloxybenzoate are dissolved in 10 g of toluene, and the reaction mixture, together with 100 ppm of dicyclopentadienylplatinum dichloride, is refluxed for 1 hour and then cooled to 50° C. 0.93 g (2,75 mmol) (55 mol %) of 4-methacryloyloxyphenyl 4-allyloxybenzoate, 0.12 g (0.25 mmol) (5 mol %) of isomannide bis(4-allyloxybenzoate) are added, and the mixture is stirred at 70° C. for 1 hour. The solvent is distilled off in vacuo, giving 2.37 g of an organosiloxane.

2.0 g of this organosiloxane are dissolved in 10 ml of dichloromethane, and 0.86 g of cholesterol methacrylate is added to the solution. The solvent is subsequently distilled off in vacuo, giving 2.86 g of a novel mixture (illustrative mixture 1).

Preparation of illustrative mixture 2

1.36 g (4.53 mmol) of pentamethylcyclopentasiloxane and 4.36 g (8.0 mmol) (40 mol %) of cholesterol 4-allyloxybenzoate are dissolved in 30 g of toluene, and the reaction mixture, together with 100 ppm of dicyclopentadienyiplatinum dichloride, is refluxed for 1 hour and then cooled to 50° C. 3.72 g (11.0 mmol) (55 mol %) of 4-methacryloyloxyphenyl 4-allyloxybenzoate and 0.46 g (1.0 mmol) (5 mol %) of isomannide bis(4-allyloxybenzoate) are added, and the mixture is stirred at 70° C. for 1 hour. The solvent is distilled off in vacuo, giving 10.13 g of an organosiloxane.

3.5 g of this organosiloxane are dissolved in 10 ml of dichloromethane, and 1.5 g of cholesterol methacrylate are added to the solution. The solvent is subsequently distilled off in vacuo, giving 5.0 g of a novel mixture (illustrative mixture 2).

Preparation of illustrative mixture 3

1.36 g (4.53 mmol) of pentamethylcyclopentasiloxane and 4.36 g (8.0 mmol) (40 mol %) of cholesterol 4-allyloxybenzoate are dissolved in 30 g of toluene, and the reaction mixture, together with 100 ppm of dicyclopentadienylplatinum dichloride, is refluxed for 1 hour and then cooled to 50° C. 3.72 g (11.0 mmol) (55 mol %) of 4-methacryloyloxyphenyl 4-allyloxybenzoate and 0.46 g (1.0 mmol) (5 mol %) of isomannide bis(4-allyloxybenzoate) are added, and the mixture is stirred at 70° C. for 1 hour. The solvent is distilled off in vacuo, giving 10.13 g of an organosiloxane.

3.5 g of this organosiloxane are mixed with 1.5 g of cholesterol methacrylate and 0.1 g of isomannide bis(4-allyloxybenzoate), and the mixture is homogenized at 100° C. for 10 minutes, giving 5.0 g of a novel mixture (illustrative mixture 3).

Preparation of illustrative mixture 4

0.68 g (2.27 mmol) of pentamethylcyclopentasiloxane, 1.64 g (3.0 mmol) (30 mol %) of doresterol 4-allyloxybenzoate and 0.61 g (1.5 mmol) (15 mol %) of 4-methoxyphenyl 4-(4-allyloxybenzoyloxy)benzoate are dissolved in 15 g of toluene, and the reaction mixture, together with 100 ppm of dicyclopentadienylplatinum dichloride, is refluxed for 1 hour and cooled to 50° C. 1.69 g (5.0 mmol) (50 mol %) of 4-methacryloyloxyphenyl 4-allyloxybenzoate and 0.23 g (0.5 mmol) (5 mol %) of isosorbide bis(4-allyloxybenzoate) are added, and the mixture is stirred at 70° C. for 1 hour. The solvent is distilled off in vacuo, giving 4.92 g of an organo-siloxane.

3.5 g of this organosiloxane are dissolved in 10 ml of dichloromethane, and 70 mg of isosorbide bis(4-allyloxybenzoate) are added to the solution. The solvent is subsequently distilled off in vacuo, giving 3.57 g of a novel mixture (illustrative mixture 4).

EXAMPLE 3

Production of the novel films

Illustrative film 1

Two quartz glass plates were provided with an alignment layer of polyvinyl alcohol, which was rubbed unidirectionally with a velvet cloth. 1% by weight of 2-methyl-1-[4-(methylthio)phenyl]-2-morpholino-1-propanone (obtainable under the name Irgacure® 907 from Ciba-Geigy AG) was admixed with illustrative mixture 1. A small amount of this mixture was applied at 90° C. to the alignment layer of one of the plates and covered with the second plate. The liquid-crystal mixture was distributed by applying uniform pressure to the plates until an approximately 10 $\mu$m film remained between the alignment layers. After five minutes, the film was polymerized by irradiation with UV-A light (approximately 100 mW/cm$^2$ for 15 sec.). The glass plates were subsequently separated from one another. A crosslinked, clear film which was colorless in visible light remained on one of the plates. A selective reflection of left-handed helical UV light at a wavelength of 314 nm was detected on both sides of the film in a UV spectrometer. The half-value width of the reflection band was 21 nm. For visible white light, a refractive index anisotropy of $\Delta n=-0.04$ was measured in the temperature range from 20° C. to 100° C.

Illustrative film 2

1% by weight of 2-methyl-1-[4-(methylthio)phenyl]-2-morpholino-1-propanone (Irgacure® 907, Ciba-Geigy) was admixed with illustrative mixture 2. As described for illustrative film 1 above, a crosslinked, clear film which was colorless in visible light was produced between quartz glass plates. A selective reflection of left-handed helical UV light at a wavelength of 315 nm was detected in a UV spectrometer. The half-value width of the reflection band was 22 nm. The film had significant refractive-index anisotropy. Uniform darkening occurred between crossed polarizers on parallel alignment with the polarizer plane and remained unchanged on rotation about the surface perpendicular of the film. When the film was tilted about an axis in the film plane, the brightness of the transmitted light increased.

Illustrative film 3

1% by weight of 2-methyl-1-[4-(methylthio)-phenyl]-2-morpholino-1-propanone (Irgacure® 907, Ciba-Geigy) was admixed with illustrative mixture 3. As described for illustrative film 1, a crosslinked film was produced between quartz glass plates. The glass plates were subsequently separated from one another. A clear film which was colorless in visible light and had significant refractive-index anisotropy remained on one of the plates. Uniform darkening occurred between crossed polarizers on parallel alignment with the polarizer plane and remained unchanged on rotation about the surface perpendicular of the film. When the film was tilted about an axis in the film plane, the brightness of the transmitted light increased. A selective reflection of left-handed helical UV light at a wavelength of 295 nm was detected on the free side of the film in a UV spectrometer. The half-value width of the reflection band was 17 nm.

Illustrative film 4

1% by weight of 2-methyl-1-[4-(methylthio)-phenyl]-2-morpholino-1-propanone (Irgacure® 907, Ciba-Geigy) was admixed with illustrative mixture 4. As described for illustrative film 1, a crosslinked film was produced between quartz glass plates. To this end, an alignment temperature of 60° C. was set. The glass plates were subsequently separated from one another. A clear film which was colorless in visible light and had significant refractive-index anisotropy remained on one of the plates. Uniform darkening occurred between crossed polarizers on parallel alignment with the polarizer plane and remained unchanged on rotation about the surface perpendicular of the film. When the film was tilted about an axis in the film plane, the brightness of the transmitted light increased. A selective reflection of right-handed helical UV light at a wavelength of 283 nm was detected on the free side of the film in a UV spectrometer. The half-value width of the reflection band was 18 nm.

EXAMPLE 4

Production of an imaging element for UV light

Figures 1A, 1B, 1C:
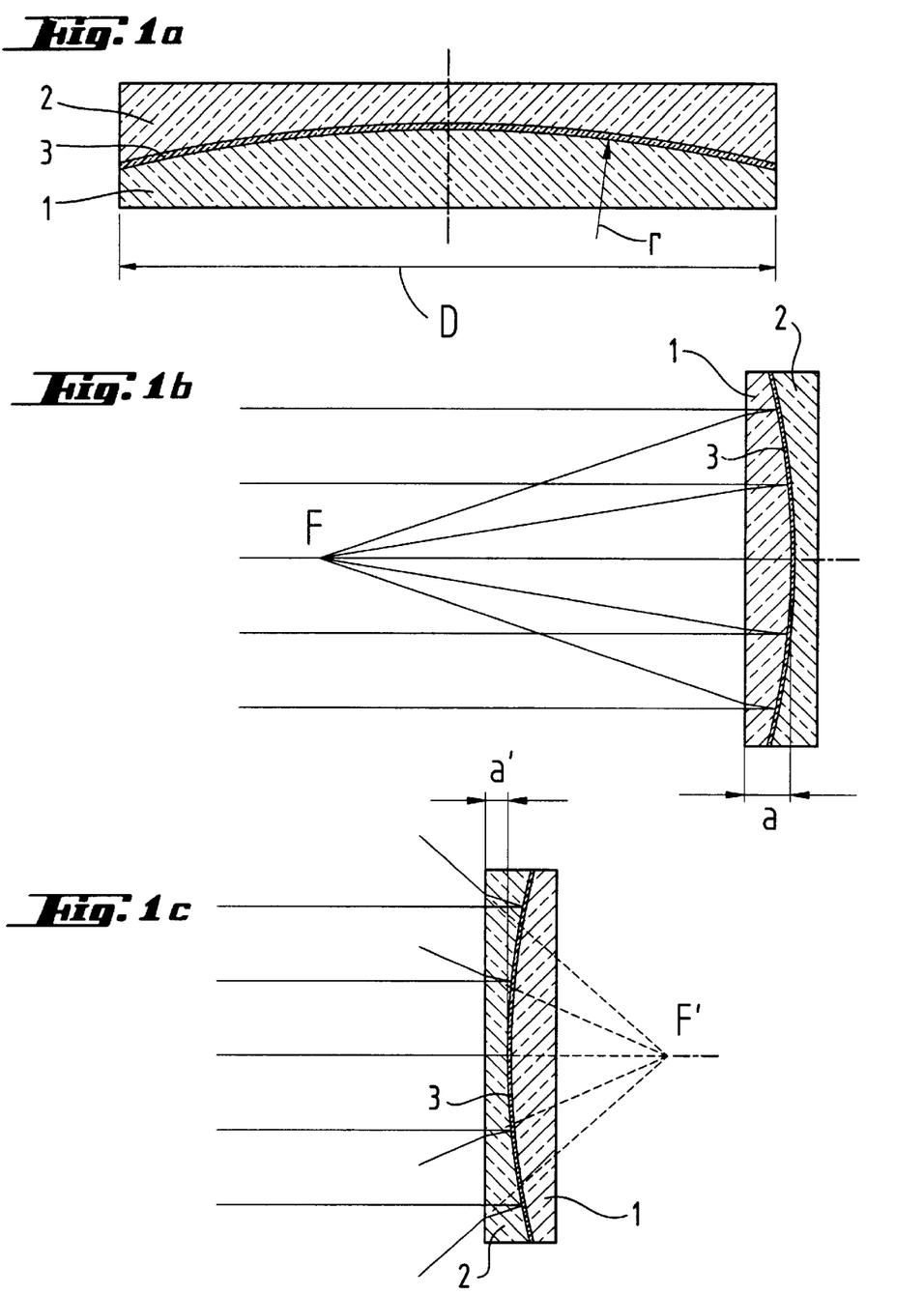
FIG. 1a) shows a section through the rotationally symmetrical element from Example 4.
FIG. 1b) shows the ray path when the element from FIG. 1a) is used as a concave mirror.
FIG. 1c) shows the ray path when the element from FIG. 1a) is used as a convex mirror.

A UV-reflective layer ((3) in FIG. 1(a)) was produced between a planoconvex ((1) in FIG. 1(a)) and planoconcave ((2) in FIG. 1(a)) spherical quartz-glass lens (diameter D=50 mm, radius of curvature r=103.7 mm, refractive index n=1.46) having focal lengths of 200 mm and −200 mm which were provided with alignment layers of polyvinyl alcohol. A novel liquid-crystal mixture having a reflection wavelength of 295 nm as for illustrative film 3 was used for this purpose. The imaging properties for left-handed helical-polarized light from the reflection band are those of a spherical concave mirror (cf. FIG. 1(b) and 1(c)). In a free concave mirror, the focal length for rays close to the axis on the concave side is r/2 and −r/2 for the convex side. The glass coating of the lens substrate introduces an additional refractive interface to the ray path, so that the focal length is calculated in accordance with the equation $$f_a = a + (r/2 - a)/n \quad (1)$$

as being 37.4 mm for the concave mirror (a=6 mm) and −34.9 mm for the convex mirror (a=−2 mm).

EXAMPLE 5

Production and use of CLC platelets

The crosslinked illustrative film 3 open on one side was scraped off the glass substrate using a knife blade. The particles which remained were ground to a mean particle diameter of about 100 nm. 20 parts by weight of the resultant colorless CLC platelets were admixed with 78 parts by weight of liquid-crystalline siloxane (obtainable as CS4000A from Wacker-Chemie GmbH, Munich) and 2 parts by weight of photoinitiator (obtainable as Irgacure® 907 from Ciba-Geigy AG) at 140° C. The mixture was applied as an approximately 40 μm film to a hot glass plate at about 110° C. using a knife coater. A polyethylene terephthalate film (obtainable from Hoechst AG, Films Division, Wiesbaden) was applied to this film by roller. By shearing the film during application of the mixture and during roller-application of the polyethylene terephthalate film, the pigment particles were aligned predominantly parallel to the film surface. The film was crosslinked photochemically by exposure to UV-A radiation (50 mW/cm² for 30 s). The polyethylene terephthalate film was subsequently peeled off from the crosslinked siloxane layer. A reflection at a wavelength of 295 nm was detected on the free side of the film in a UV spectrometer. The film, which was colorless and transparent to visible light, had clear refractive-index anisotropy. Uniform darkening occurred between crossed polarizers on parallel alignment with the polarizer plane and remained unchanged on rotation about the surface perpendicular of the film. When the film was tilted about an axis in the film plane, the brightness of the transmitted light increased.

EXAMPLE 6

Use of a retardation layer in an LCD display

The front polarizer was removed from a commercially available TFT liquid-crystal display. Illustrative film 3, open on one side, was installed between the front polarizer and the switchable LC cell. At a perpendicular viewing direction of the display modified in this way, no change occurred compared with the original state. At an oblique viewing direction, a change in the contrast was observed.

While several embodiments of the present invention have been shown and described, it is to be understood that many changes and modifications may be made thereunto without departing from the spirit and scope of the invention as defined in the appended claims.

What is claimed is:

1. A liquid-crystalline material having a cholesteric phase with a pitch of less than 400 nm, comprising
   (a) liquid-crystalline organosiloxane containing dianhydrohexitol derivatives as chiral groups, and
   (b) a chiral monomeric additive which induces the same helicality as the said liquid-crystalline organosiloxane.

2. A liquid-crystalline material as claimed in claim 1, wherein the liquid-crystalline organosiloxane contains, per molecule, at least one Si-C-bonded dianhydrohexitol derivative of the general formula (1)

$$M^1\text{—hexitol—}M^2 \quad (1)$$

as chiral component, where hexitol is a dianhydrohexitol derivative, $M^1$ is a radical of the general formula (2), $M^2$ is a radical of the general formula (2) or a radical of the general formula (3), where, in the above general formulae (2) and (3), $R^1$ and $R^3$ are each a radical of the formula $C_nH_m$, in which one or more non-adjacent methylene units may be replaced by oxygen atoms or dimethylsilyl radicals, $R^2$ is a polymerizable ethylenically unsaturated group or alkoxysiloxy group or cholesteryl radical, doristerol radical, halogen atom, hydrogen atom, hydroxyl, nitrile or trialkylsiloxy group whose alkyl radicals each have 1 to 8 carbon atoms, $A^1$, $A^2$, $A^3$ and $A^4$ are identical or different divalent radicals, namely 1,4-phenylene, 1,4-cycloyhexylene, substituted arylene having 1 to 10 carbon atoms, substituted cycloalkylene having 1 to 10 carbon atoms or heteroarylene having 1 to 10 carbon atoms, $X^1$ and $X^2$ are identical or different divalent radicals from the group consisting of —OCO—, —NHCO—, —CO— and a radical $R^1$, $Z^1$ and $Z^2$ are identical or different divalent radicals from the group consisting of —(CH$_2$)$_q$—, —COO—, —CH=CH—, —N=N—, —N=N(O)—, —OCO—, —CH$_2$CO—, —COCH$_2$—, —CH$_2$—O—, —O—CH$_2$—, —CH$_2$—NH—, —NH—CH$_2$—, —CONH—, —NHCO—, —N=CH— and —CH=N—, b, c and d are identical or different integers, each having a value of 0, 1, 2 or 3, n is an integer having a value of from 0 to 20, m has the value 2n or, if n is at least 2, can also have the value (2n−2), q is an integer having a value of 1, 2 or 3, r and s are each an integer having a value of 0 or 1.

3. A liquid-crystalline material as claimed in claim 2, wherein the liquid-crystalline organosiloxane is built up in accordance with the general formulae (4) to (6)

in which

B is a radical of the general formula (1) or, a radical of the general formula (7)

$$R^4—(A^5)_x—Z^3_t—(A^6)_y—Z^4_u—(A^7)_z—A^8 \quad (7)$$

where, in the above formulae (4) to (7), the radicals R are identical or different, unsubstituted or substituted $C^1$- to $C^{18}$-hydrocarbon radicals, e and g are each an integer having a value of from 1 to 100, f, h, i and j are each an integer having a value of from 0 to 100, $R^4$ is as defined for $R^1$, $A^5$, $A^6$ and $A^7$ are as defined for $A^1$, $Z^3$ and $Z^4$ are as defined for $Z^1$, $A^8$ is a saturated or olefinically unsaturated, unsubstituted or substituted alkyl, alkoxy or cycloalkyl radical, in each case having 1–16 carbon atoms, cholestan radical, cholesteryl radical, doristerol radical, halogen atom, hydrogen atom, hydroxyl, nitrile, (meth)acryloxy, (meth)acryloxyethyleneoxy, (meth)acryloxydi(ethyleneoxy), (meth)acryloxytri-(ethyleneoxy), R- or S-tetrahydrofurancarboxylate or trialkyl- or trialkoxysiloxy group whose alkyl or alkoxy radicals have 1 to 8 carbon atoms, x, y and z are identical or different integers, each having a value of 0, 1, 2 or 3, and t and u are as defined for r, with the proviso that the sum e+f is at least 2.

4. A liquid-crystalline material as claimed in claim 2, which contain, as chiral, a monomeric additive which induce the same helicality as the respective liquid-crystalline organosiloxane, compounds of the formula (19) or (20)

in which $M^4$ and $M^5$ are a radical of the general formula (2) or a radical of the general formula (3), and chir is a chiral radical, selected from the group consisting of a cholesteryl, dihydrocholesteryl, doristeryl, cholestadienyl, stigmasterol and hexitol, $M^2$, $R^1$, $R^2$, $R^3$, $A^1$, $A^2$, $A^1$, $A^4$, $X^1$, $X^2$, $Z^1$, $Z^2$, a, b, c, d, r and s are as defined above.

5. A process for the preparation of a liquid-crystalline material, said liquid-crystalline material having a cholesteric phase with a pitch of less than 400 nm, comprising
(a) a liquid-crystalline organosiloxane containing dianhydrohexitol derivatives as chiral groups, and
(b) a chiral monomeric additive which induces the same helicality as the said liquid-crystalline organosiloxane, which process comprises combining an individual liquid-crystalline organosiloxane of component (a) with an individual chiral monomeric additive of component (b) in the solid phase.

6. A process for the preparation of a liquid-crystalline material, said liquid-crystalline material having a cholesteric phase with a pitch of less than 400 nm, comprising
(a) a liquid-crystalline organosiloxane containing dianhydrohexitol derivatives as chiral groups, and
(b) a chiral monomeric additive which induces the same helicality as the said liquid-crystalline organosiloxane, which process comprises combining an individual liquid-crystalline organosiloxane of component (a) with an individual chiral monomeric additive of component (b) in the liquid phase.

7. A process for the preparation of a liquid-crystalline material, said liquid-crystalline material having a cholesteric phase with a pitch of less than 400 nm, comprising
(a) a liquid-crystalline organosiloxane containing dianhydrohexitol derivatives as chiral groups, and
(b) a chiral monomeric additive which induces the same helicality as the said liquid-crystalline organosiloxane, which process comprises combining an individual liquid-crystalline organosiloxane of component (a) with an individual chiral monomeric additive of component (b) in solution.

8. An optically anisotropic film, which contains a liquid-crystalline material, as claimed in claim 1.

9. An optically anisotropic CLC platelet, which contains a liquid-crystalline material, as claimed in claim 1.

10. An optical element, which contains a liquid-crystalline material, as claimed in claim 1.

11. A liquid-crystal display device, which includes at least one optically anisotropic film as claimed in claim 8.

12. A liquid-crystal display device, which includes at least one optically anisotropic CLC platelet as claimed in claim 9.

13. A liquid-crystal display device, which includes at least one optical element as claimed in claim 10.

14. A marking which contains a liquid-crystalline material as claimed in claim 1.

15. A marking which contains a liquid-crystalline material comprising said film as claimed in claim 8.

16. A marking which contains liquid-crystalline materials comprising said platelet as claimed in claim 9.

* * * * *